Feb. 22, 1955 R. O. RUBEL, JR Plant Pat. 1,351
CAMELLIA PLANT
Filed Sept. 16, 1953
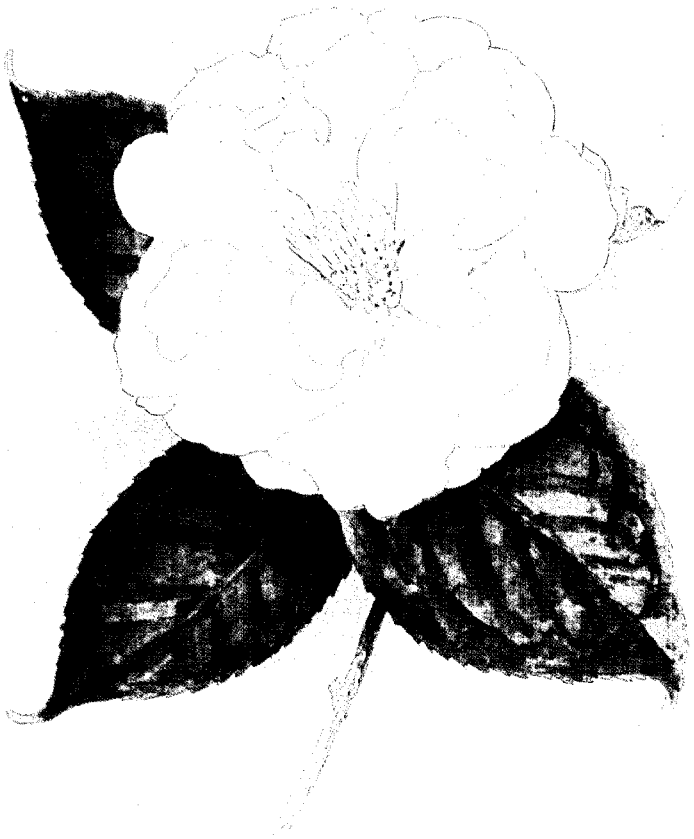
WITNESS
Addison E. Avery
INVENTOR
ROBERT O. RUBEL, JR.,
by Rummler, Rummler & Snow,
ATTYS.

United States Patent Office

Plant Pat. 1,351
Patented Feb. 22, 1955

1,351

CAMELLIA PLANT

Robert O. Rubel, Jr., Mobile, Ala., assignor to Cliff Harris, Mobile, Ala.

Application September 16, 1953, Serial No. 380,636

1 Claim. (Cl. 47—60)

This invention relates to a new and distinct variety of camellia plant resulting from the harvesting and planting of mixed seeds from selected plants, growing many resulting seedlings, and selecting and developing from these plants that have desired characteristics. The herein-described variety originated from such procedure as a seedling of unknown parentage, which was grown at my nursery in Mobile, Alabama.

Being in the japonica species, the growing habits of this variety correspond to most midseason blooming camellias. The opened flower is distinctly different from any other known to me. However, it resembles the *Camellia reticulata* variety "Captain Rames" (not patented). The characteristic growth of this new variety is vigorous and compact and, although the bloom resembles the reticulata, its growth is not characteristic of the reticulata, which is rampant.

The flower is large and high, unicolored variably from brilliant salmon pink to light rose pink. The outer petals are obovate, lobed at the apex, and attenuate at the base. The central portion of the flower is composed of few petaloids intermixed and grouped with stamens in fascicles. The inner petals are obovate, wrinkled, creped and folded. The leaves are glossy, coriaceous, obovate, with cuneate base, acute apex, and serrated edges.

The accompanying painting shows blooms at different stages of maturity, and foliage.

Color designations according to Maerz and Paul's Dictionary of Color are as follows:

| Part | Plate | Ltr. | No. |
|---|---|---|---|
| Flower, lightest tone of outer areas | 1 | A | 3. |
| shading into | 1 | I | 3. |
| shading into darkest in areas | 3 | J | 4. |
| Pistils, stamens and stigmas | 9 | L | 7. |
| Leaves: | | | |
| Top of leaf | 23 | L | 5 plus yellow. |
| Under side of leaf | 22 | L | 6 plus yellow. |
| Stems | 7 | C | 12. |

A detailed description follows:

Parentage: Seedling. Seed parents: unknown.
Classification: *Camellia japonica.*

It is the result of selection procedures.

This plant was asexually reproduced by me at Mobile, Alabama from cuttings and grafting.

Flower:
- *Recurrent.*—Yes.
- *Blooms.*—Midseason to late. Opens freely and has exceptional keeping qualities on plant when grown in partial shade, and as a cut flower.
- *Other habits.*—Normally unicolored pink but has produced a sport variegated with white.
- *Size.*—Maximum size 5 in. (12.5 cm.) in diameter x 2 in. (5 cm.) high.
- *Borne.*—Singly and double.
- *Shape.*—Incomplete double with high center.
- *Fragrant.*—No.
- *Petals.*—Number—14 outer petals, in total of approximately 30 to 35 petals and petaloids.
- *Form.*—Obovate, lobed at apex, attenuate at base.
- *Size.*—2 in. (5 cm.) long and 1 9/16 in. (4 cm.) wide.
- *Color.*—Unicolored, variable from brilliant salmon pink to light rose pink.
- *Texture.*—Leathery.
- *Appearance.*—Satiny.
- *Lasting quality.*—On plant, excellent. As a cut flower, excellent.

Genital organs:
- *Stamens.*—Length—¾ in. (2 cm.). Number—approximately 177. Color—tinted rose. Arrangement—central, intermixed with petals and petaloids. Pollen—yellow in color.
- *Styles.*—Number—4. Length 1 3/16 in. (3 cm.).
- *Ovaries.*—Yes.

Bud:
- *Size.*—Large 1 3/16 in. (3 cm.) long and about 13/16 in. (2 cm.) in diameter.
- *Form.*—Globular.
- *Color.*—When sepals first divide—light green; when sepals begin to unfurl—light green.
- *Sepals.*—Hooded over bud. 9 to 11 in number.
- *Calyx.*—Size: large, 1 13/16 in. (4.5 cm.) across.
- *Form.*—Cupped.
- *Aspect.*—Smooth. Does not split.

Plant:
- *Form.*—Bush, upright.
- *Height.*—Depends on age.
- *Growth.*—Compact, vigorous and branching.

Foliage:
- *Quantity.*—Abundant.
- *Size of leaf.*—2 15/16 in. (7.5 cm.) long and 1 13/16–2⅝ in. (4.5–6 cm.) wide.
- *Shape of leaf.*—Ovate. Base cuneate, apex acute, serrated edges.
- *Texture.*—Coriaceous, glossy.
- *Color.*—Upper side, blue-green. Under side, yellow-green.
- *Petioles.*—Length: ½ in. (1.2 cm.).

Fruit:
- *Fertile.*—Yes.
- *Shape.*—Usually ovoid.
- *Color.*—At maturity, green.

I claim:

A new and distinct variety of camellia plant, substantially as shown and described, characterized by the color and shape of its bloom, and its vigorous and compact growth.

No references cited.